United States Patent [19]

Colclough

[11] Patent Number: 4,859,353
[45] Date of Patent: Aug. 22, 1989

[54] SULPHUR-CONTAINING BORATE ESTERS

[75] Inventor: Terence Colclough, Abingdon, United Kingdom

[73] Assignee: Exxon Chemical Patents Inc., Linden, N.J.

[21] Appl. No.: 176,444

[22] Filed: Apr. 1, 1988

[30] Foreign Application Priority Data

Apr. 2, 1987 [GB] United Kingdom ............... 8707833

[51] Int. Cl.$^4$ ............... C10M 139/00; C10M 135/20
[52] U.S. Cl. .................. 252/46.3; 252/47.5; 252/48.4; 252/49.6; 558/288; 558/290; 558/291; 558/293
[58] Field of Search .......... 252/46.3, 49.6, 47.5, 252/48.4; 558/288, 290, 291, 293

[56] References Cited

U.S. PATENT DOCUMENTS

| | | | |
|---|---|---|---|
| 2,526,506 | 10/1950 | Rogers et al. | 252/46.3 |
| 2,866,811 | 12/1958 | Irish et al. | 260/462 |
| 2,894,020 | 7/1959 | McManimie | 260/462 |
| 3,030,196 | 4/1962 | Dykstra | 44/69 |
| 3,092,586 | 6/1963 | Dykstra | 252/46.6 |
| 3,711,412 | 1/1973 | Sawyer et al. | 252/78 |
| 4,115,286 | 9/1978 | Baldwin et al. | 558/290 |
| 4,370,248 | 1/1983 | Horodysky et al. | 252/49.6 |
| 4,374,032 | 2/1983 | Gemmill et al. | 252/49.6 |
| 4,406,802 | 9/1983 | Horodysky et al. | 252/49.6 |
| 4,440,656 | 4/1984 | Horodysky | 252/49.6 |
| 4,465,605 | 8/1984 | Horodysky et al. | 252/46.3 |
| 4,478,732 | 10/1984 | Horodysky et al. | 252/49.6 |
| 4,490,265 | 12/1984 | Holstedt et al. | 252/47.5 |
| 4,492,640 | 1/1985 | Horodysky et al. | 252/46.3 |
| 4,595,514 | 6/1986 | Holstedt et al. | 252/46.4 |
| 4,623,474 | 11/1986 | Holstedt et al. | 252/47.5 |
| 4,627,930 | 12/1986 | Holstedt et al. | 252/49.6 |
| 4,756,842 | 7/1988 | Holstedt et al. | 252/46.3 |
| 4,759,873 | 7/1988 | Audeh | 252/46.3 |
| 4,769,164 | 9/1988 | Salomon | 252/48.2 |

FOREIGN PATENT DOCUMENTS

| | | |
|---|---|---|
| 737986 | 7/1966 | Canada ................. 558/291 |
| 0024146 | 2/1981 | European Pat. Off. . |
| 0089844 | 9/1983 | European Pat. Off. . |
| 2148142 | 3/1973 | France . |
| 497291 | 6/1973 | U.S.S.R. . |
| 1232369 | 7/1968 | United Kingdom . |
| 8606092 | 10/1986 | World Int. Prop. O. . |

OTHER PUBLICATIONS

European Search Report (for the corresponding European Applic. 88/302,978).

Primary Examiner—William R. Dixon, Jr.
Attorney, Agent, or Firm—J. B. Murray, Jr.

[57] ABSTRACT

Sulphur-containing borate esters for use in lubricants appropriate to modern oil requirements with reduced or zero amounts of phosphorous and without the need for large amounts and/or expensive forms of antioxidant and additional anti-wear additives are of the formula:

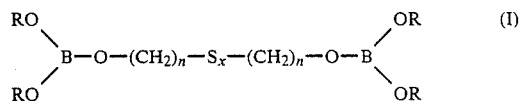

wherein each R is a hydrocarbyl group optionally substituted by one or more —XR″ group, or the two R groups attached to one boron represent a group —(R′CH)$_m$—, x is 1 or 2, each n is from 1 to 6, each m is from 2 to 4 and each R′ is hydrogen, and —XR″ group, or a hydrocarbyl radical optionally substituted by one or more —XR″ group, X is O, S or NR″ and R″ is hydrogen, a hydrocarbyl radical or a hydrocarbylcarbonyl group.

18 Claims, No Drawings

SULPHUR-CONTAINING BORATE ESTERS

The present invention relates to sulphur-containing borate esters, and their use in lubricating compositions, especially crankcase lubricants for automobiles and trucks.

The esters of the invention may be used as anti-oxidants and/or corrosion inhibitors and/or anti-wear additives and/or friction modifiers in a wide range of oleaginous compositions. Various borate esters have been used as lubricant additives such as corrosion inhibitors and/or anti-wear additives, as disclosed in US-A-4440656, US-A-3030196, US-A-3711412, US-A-2866811 and WO-A-8606092, but some of these borates are difficult to handle because of their tendency to hydrolyse. Levels of phosphorus have typically been on the order of 1.0% but for some applications it is desirable to reduce phosphorus levels to below 0.05 wt % or even remove it altogether. However, zinc dialkyl dithiophosphates (ZDDP) and other phosphorus containing additives have been widely used as anti-wear and/or anti-oxidant additives and simply reducing or removing such components results in lubricants with poor engine performance. The esters of the invention may be useful in such low phosphorus lubricants to replace all or part of the ZDDP.

EP-A-24146 discloses lubricant compositions containing an ashless dispersant and/or polymeric viscosity index improver dispersant and copper which may be in the form of a dithiocarbamate, but requires the presence of zinc and from 0.01 to 0.5 wt % phosphorus. Borate esters are an optional component.

EP-189844 describes the reaction products of 4,4'-methylene bis(2,6-di-t-butyl phenol) and tri-sec-$C_{4-12}$ alkyl orthoborate and their use in lubricants.

US-A-4490265, US-A-4627930 and US-A-4623474 describe lubricating oils comprising boron-containing heterocyclic compounds which may be in the form of a metal salt.

SU-497291 is reported in Derwent Abstract No. 37592Y/21 to describe mixed sulphur-containing orthoborates of the formula: $R_1SCH_2OB(OR_2)_2$ where $R_1$ is alkyl or aryl and $R_2$ is alkyl as lubricant additives.

US-A-4465605 describes borated trihydroxy hydrocarbyl sulphides as friction reducing or antioxidant additives. US-A-4492640 describes borated mixtures of long chain alcohols and trihydroxy hydrocarbyl sulphides to reduce friction and fuel consumption in engines.

Borated hydroxy-substituted aromatic comounds as lubricant additives are described in US-A-4370248, US-A-4374032, US-A-4406802 and US-A-4478732 to form compounds containing boron but no sulphur.

The invention seeks to provide sulphur-containing borate esters for use in lubricant appropriate to modern oil requirements with reduced or zero amounts of phosphorus and without the need for large amounts and/or expensive forms of antioxidant and additional anti-wear additives.

In one aspect this invention provides the sulphur-containing borate esters of the formula:

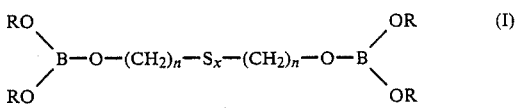

(wherein each R is s hydrocarbyl group optionally substituted by one or more —XR" group, or the two R groups attached to one boron represent a group —$(R'_2C)_m$—, x is from 1 to 4, each n is from 1 to 6, each m is from 2 to 4 and each R' is hydrogen, an —XR" group, or a hydrocarbyl radical optionally substituted by one or more —XR" group, X is O, S or NR" or two groups R'together form an alicyclic or heterocyclic ring, and R" is hydrogen, a hydrocarbyl radical or a hydrocarbylcarbonyl group) and mixtures and polymeric forms thereof.

The hydocarbyl groups may be alkyl, alkenyl aryl, alkaryl or aralkyl groups. The presence of groups such as oleoyl and linear long chain alkyl groups is desirable for some applications as it may provide improved friction performance.

In a preferred aspect each pair of substituents R represent a —$(R'_2$—$C)_m$—group and R' is hydrogen, an alkyl group, or an esterified hydroxy group —i.e. a hydrocarbylcarboxy group (X=O; R"=hydrocarbylcarbonyl), preferably an alkylcarboxy group. When two groups R' together form an alicyclic or heterocyclic ring this is preferably an oxazoline or imidazoline which may itself be substituted, for example by a hydrocarbyl group.

The integer n is preferably from 2 to 4 and most preferably 2. The integer x is very preferably 2 so that the compounds are disulphide derivatives. When R represents the —$(R'CH)_m$—group, integer m is very preferably 3. Thus, a highly preferred class of compounds are those of the formula:

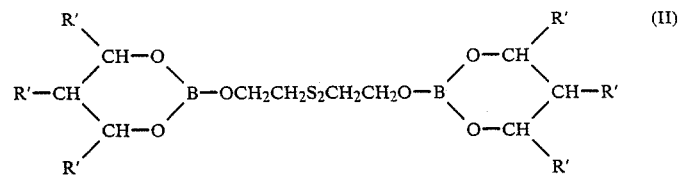

where each R' is preferably independently chosen from hydrogen, alkyl, hydroxy and alkylcarboxy.

Particularly preferred compounds are those of the formulae:

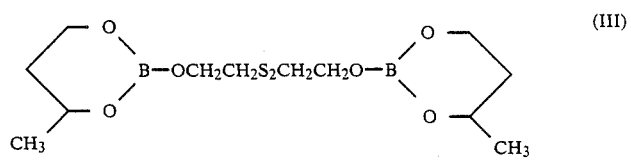

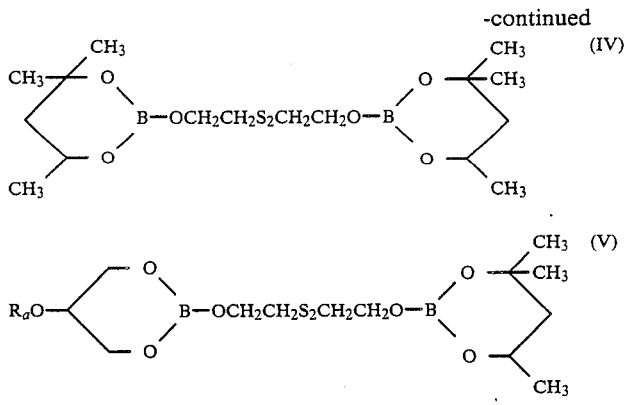

where $R_a$ is an oleoyl group.

Another preferred group of compounds are those wherein each R is an alkyl group preferably having from 1 to 20 carbon atoms.

The compounds of the invention may conveniently be stored as a concentrate together with a dispersant (as described hereinafter) to reduce risk of unwanted hydrolysis.

The compounds of general formula I may be prepared by reacting a dihydroxy alkyl sulphide of the general formula:

$$HO(CH_2)_n-S_x-(CH_2)_nOH \qquad (VI)$$

with one or more appropriate alcohols ROH or diols of the formula $HO(R'-CH)_mOH$ and boric acid. This reaction generally requires heating, typically to a temperature of from 20° C. to the boiling point of the reaction mixture. If a higher temperature than the normal boiling point is required the reaction vessel may be pressurized. Preferably toluene is used in the reaction mixture to remove water as an azeotrope, and the temperature of the reaction then typically reaches 120° C.—140° C.

Thus, to prepare the preferred compound of general formula III, dihydroxydiethyldisulphide (DHDS) is reacted with boric acid and butane-1,3-diol. Similarly to prepare the compound of general formula IV the diolis 2-methyl-pentane-2,4-diol, while 2-methyl-pentane-2,4-diol and glyceryl monooleate is used to prepare the compound of general formula V in each case in reaction with boric acid and DHDS. This latter preparation is advantageous in introducing friction modifier properties into the molecule.

Examples of alcohols and diols for use in the process which contain —XR″ substituents are hydroxyalkyl sulphides and thioglycerol.

An example of a diol containing a heterocyclic ring is a substituted oxazoline, such as prepared by reacting tris(hydroxymethyl)-aminomethane with a carboxylic acid or a hydroxyalkyl or hydroxyalkenyl hydrocarbyl imidazoline.

This invention also relates to the use of the novel sulphur-containing borate esters in oleaginous compositions for use as lubricants, power transmission fluids or fuels, and thus provides such compositions comprising a major amount of an oil and a minor amount of a compound of the invention. The invention is particularly concerned with lubricating compositions comprising the compounds of the invention. Such compositions preferably contain from 0.01 to 10 wt % of the compound of general formula I, more preferably from 0.1 to 5 wt %.

In another aspect, this invention provides a low phosphorus lubricant composition comprising a major amount of a lubricating oil, 5 to 500 parts per million by weight (ppm) of added copper present in oil-soluble form, one or more compounds of general formula I, such low phosphorus compositions preferably containing less than 0.05 wt % phosphorus, more preferably containing less than 0.01 wt % phosphorus, most preferably being substantially phosphorus-free.

In particularly preferred embodiments of the invention, the lubricant composition will also contain oil-soluble sulphur-containing compound and/or one or more ashless dispersants and/or one or more bearing corrosion inhibitor and/or one or more viscosity index improver dispersants and/or one or more overbased additives which function as antacid and anti-rust agents, such as overbased calcium or magnesium sulphonates or phenates.

Copper acts as an anti-oxidant in the amounts specified above. At unduly low concentrations, the anti-oxidant effect may not be sufficient for some applications, while at unduly high concentrations the level of ash will be increased. The amount of added copper in the compositions will preferably be 10 to 200 ppm, e.g. 60 to 200 ppm.

The ability of the compositions of the invention comprising the compounds of the invention, low amounts of oil-soluble copper compounds and very low or zero amounts of phosphorus to provide adequate antioxidant and antiwear performance for the stringent requirements of modern engine tests is surprising. Copper is known to act in many situations as an oxidation promoter or catalyst, and closely related metals, such as cobalt and chromium, are not effective lubricant antioxidants. EP-A-24146 teaches the presence of at least 0.01 wt % of each of phosphorus and zinc.

It is also surprising that the copper compound functions effectively in compositions which may contain zinc and other metal compounds, such as calcium or magnesium overbased additives, which have an inherent pro-oxidant activity.

The copper compounds used as anti-oxidants in this invention may be chosen from those described in EP-A-24146 as suitable for lubricants provided that the copper compounds are substantially free of phosphorus.

Thus, the copper may be blended into the oil as the oil-soluble copper salt of a synthetic or natural carboxylic acid. Examples of suitable carboxylic acids include $C_{10}$ to $C_{18}$ fatty acids such as stearic or palmitic acid, unsaturated acids such as oleic acid, branched carboxylic acids such as naphthenic acids of molecular weight from 200 to 500, neodecanoic or 2-ethylhexanoic acid and alkyl or alkenyl substituted dicarboxylic acids such as polyalkene substituted succinic acids, e.g. octadecenyl succinic acids, dodecenyl succinic acids and polyisobutenyl succinic acids.

The copper may be blended into the oil as oil-soluble copper dithiophosphates of the general formula $(RO(R'O)PSS)_2Cu$ or copper dithiocarbamates of the general formula $(RR'NCSS)_nCu$, where n is 1 or 2 and R and R' are the same or different hydrocarbyl radicals containing 1 to 18, preferably 2 to 12 carbon atoms such as alkyl, alkenyl, aryl, aralkyl, alkaryl and cycloalkyl radicals. Copper sulphonates, phenates, and acetylacetonates may also be used.

Alternatively the copper may be introduced in the oil in an oil-insoluble form provided that in the finished lubricant composition the copper is in the form of a oil-soluble compound. The term "added copper" is intended to exclude copper present in the oil as a result of accumulation of copper in the oil during use, e.g. by wear or corrosion of copper-containing components.

The lubricant compositions of the invention may also contain an additional oil-soluble sulphur compound. One preferred class of such sulphur compounds are the dithiocarbamates, preferably of the formula: $(RR'NCSS)_n M$, wherein R, R' and n are as defined hereinbefore and M is a suitable metal such as zinc, molybdenum or (as indicated above) copper or a hydrocarbyl radical. Preferred dithiocarbamates are dialky dithiocarbamates preferably containing 2 to 12 carbon atoms such as diamyl dithiocarbamates. A particularly preferred compound is zinc diamyl dithiocarbamate.

Sulphus may also be introduced as a mercaptide particularly the mercaptides or aliphatic mercaptans, sulphurized unsaturated organic compounds including sulphurized olefins, sulphurized Diels-Alder adducts (e.g. US-A-3632566, US-A-3498919 and US-E-27331) and particularly sulphurized unsaturated alcohols, and esters such as sperm oil substitutes, sulphides including di- and polysulphides, thioethers, thiophenols, xanthates, sulphurized esters, thioesters, thioamides, thiazoles such as benzothiazoles and particularly mercaptobenzothiazoles and thiadiazoles.

Mineral lubricating oils contain sulphur, whereas synthetic oils may be sulphur-free, so that the amount of sulphur added as a sulphur-containing compound varies according to the basestock, the sulphur contents of other components in the lubricating composition, and the total amount of sulphur desired which is preferably greater than 0.5 to 1.0 wt % total sulphur. The lubricant compositions of the invention preferably contain from 0.5 to 0.7 wt % total S, and most preferably 0.1 to 0.5 wt % S are added oil-soluble sulphur-containing compound. They also may contain zinc, if so preferably 0.01 to 0.5 wt % Zn, more preferably 0.05 to 0.2 wt % Zn.

An additional bearing corrosion inhibitor may be present. This is a corrosion inhibitor effective at inhibiting corrosion effects on bearings such as Cu/Pb bearings. Examples of bearing corrosion inhibitors are borate esters particularly those of the formula:

$B(OR)_3$, $(RO)_2B-O-B(OR)_2$ or $(ROBO)_3$ and mixtures thereof (wherein R is a substituted or unsubstituted alkyl, aryl or aralkyl group.

As an alternative, there may be used as a bearing corrosion inhibitor a thiadiazole mercaptan, especially a thiadiazole polysulphide containing from 5 to 50 carbon atoms, a derivative or polymer thereof. Preferred materials are the 1,3,4 thiadiazole polysulphides such as those described in US-A-2719125, 2719126 and 3087932. Especially preferred is the compound 2,5-bis (t-octadithio)-1,3,4-thiadiazole commercially available as Amoco 150 or 2,5-bis(nonyldithio)-1,3, 4-thiadiazole available as Amoco 158. Other similar materials also suitable are described in US-A-3821236, 3904537, 4097387, 4107059, 4136043, 4188299 and 4193882. Derivatives of the 1, 3, 4-thiadiazole mercaptans may be used such as esters, condensation products with halogenated carboxylic acids, reaction products with aldehydes and amines, alcohols or mercaptans, amine salts, dithiocarbamates, reaction products with ashless dispersants (e.g. US-A-4140643 and US-A-4136043) and reaction products with sulphur halides and olefins.

These materials may be present in an amount of from 0.01 to 10 wt %, more preferably 0.1 to 5.0 wt % of the lubricant composition.

In a preferred aspect the lubricating composition further comprises:
(A) from 1 to 10 wt % of an ashless dispersant compound which is:
an ashless nitrogen or ester containing dispersant compound preferably selected from:
(i) oil soluble salts, amides, imides, oxazolines and esters, or mixtures thereof, of long chain hydrocarbon substituted mono and dicarboxylic acids or their anhydrides;
(ii) long chain aliphatic hydrocarbon having a polyamine attached directly thereto; and
(iii) Mannich condensation products formed by condensing a molar proportion of long chain hydrocarbon substituted phenol with 1 to 2.5 moles of formaldehyde and 0.5 to 2 moles of polyalkylene polyamine; wherein said long chain hydrocarbon group is a polymer of a $C_2$ to $C_5$ monoolefin, said polymer having a molecular weight of 700 to 5000; and/or
(B) from 0.3 to 10 wt %, of a nitrogen or ester containing polymeric viscosity index improver dispersant which may include
(a) polymers comprised of $C_4$ to $C_{24}$ unsaturated esters of vinyl alcohol or $C_4$ to $C_{10}$ unsaturated mono- or di-carboxylic acid with unsaturated nitrogen containing monomers having 4 to 20 carbons;
(b) polymers of $C_2$ to $C_{20}$ olefin with unsaturated $C_3$ to $C_{10}$ mono- or di-carboxylic acid neutralised with amine, hydroxy amine or alcohols; and
(c) polymers of ethylene with $C_3$ to $C_{20}$ olefin further reacted either by grafting $C_4$ to $C_{20}$ unsaturated nitrogen containing monomers thereon or by grafting an unsaturated acid onto the polymer backbone and then reacting said carboxylic acid groups with amine, hydroxy amine or alcohol.

The nitrogen containing dispersant additives are those known in the art as sludge dispersants for crankcase motor oils, e.g. such as shown in US-A-3275554, US-A-3565804, US-A-3442808, US-A-3442808, GB-A-983040 or BE-A-658236.

The most commonly used dispersants are those formed by reacting alkenyl succinic acydride, e.g. polyisobutenyl succinic anhydride, and an amine described in US-A-3202678, 3154560, 3172892, 3024195, 3024237, 3219666, 32116936 and BE-A-662875.

Alternatively the ashless dispersants may be esters derived from long chain hydrocarbon substituted carboxylic acids and from hydroxy compounds such as monohydric and polyhydric alcohols or aromatic compounds such as phenols and naphthols as prepared for example in US-A-3522179.

Hydroxyamines which can be reacted with any of the aforesaid long chain hydrocarbon substituted carboxylic acids to form dispersants include 2-amino-1-butanol, 2-amino-2-methyl-1-propanol, p-(beta-hydroxyethyl)-aniline, 2-amino-1-propanol, 3-amino-1-propanol, 2-amino-2-methyl-1 3-propane-diol, 2-amino-2-ethyl-1, 3-propanediol, N-(beta-hydroxy-propyl)-N'-(beta-aminoethyl)-piperazine, tris(hydroxymethyl) amino-methane (also known as trismethylolaminomethane), 2-amino-1-butanol, ethanolamine, beta-(beta-hydroxyethoxy)-ethylamine, and the like. Mixtures of these or similar amines can also be employed.

Preferred dispersants are those derived from polyisobutenyl succinic anhydride and polyethylene amines, e.g. tetraethylene pentamine, polyoxyethylene and polyoxypropylene amines, e.g. polyoxypropylene diamine, trismethylolaminomethane and pentaerythritol, and combinations thereof. One particularly preferred dispersant combination involves a combination of (A) polyisobutenyl succinic anhydride with (B) a hydroxy compound, e.g. pentaerythritol, (C) a polyoxyalkylene polyamine, e.g. polyoxypropylene diamine, and (D) a polyalkylene polyamine, e.g. polyethylene diamine and tetraethylene pentamine using about 0.01 to about 4 equivalents of (B) and (D) and about 0.01 to about 2 equivalents of (C) per equivalent of (A) as described in US-A-3894763. Another preferred dispersant combination involves the combination of (A) polyisobutenyl succinic anhydride with (B) a polyalkylene polyamine, e.g. tetraethylene pentamine, and (C) a polyhydric alcohol or polyhydroxy-substituted aliphatic primary amine, e.g. pentaerythritol or trismethylolaminomethane as described in US-A-3632511.

The alkenyl succinic polyamine type dispersants can be further modified with a boron compound such as boron oxide, boron halides, boron acids and ester of boron acids in an amount to provide 0.1 to 10 atomic proportions of boron per mole of the acylated nitrogen compound as generally taught in US-A-3087936 and 3254025. Mixtures of dispersants can also be used such as those described in US-A-4113639.

The oils may contain from 1.0 to 10 wt %, more preferably 2.0 to 7.0 wt % of these dispersants.

The dispersancy may be provided by 0.3 to 10% of a polymeric Viscosity Index improver dispersant, for example copolymers of alkyl methacrylates with N-vinyl pyrrolidone or dimethylaminoalkyl methacrylate, alkyl fumarate-vinyl acetate N-vinyl pyrolidine copolymers, post-grafted interpolymers of ethylene-propylene with an active monomer such as maleic anhydride which may be further reacted with an alcohol or an alkylene polyamine, such as in US-A-4149984; or styrene/maleic anhydride polymers post-reacted with alcohols and amines, ethoxylated derivatives of acrylate polymers such as in US-A-3702300.

Magnesium and/or calcium containing additives are frequently included in lubricating compositions either alone or in combination with other metal additivies such as sodium additives. These may be present for example as the metal salts of sulphonic acids, alkyl phenols, sulphurised alkyl phenols, alkyl salicylates, naphthenates, and other oil soluble mono-and di-carboxylic acids.

Highly basic alkaline earth metal alkaryl sulfonates are generally known for example in US-A-3150088 and 3150089. For the purposes of this invention, a preferred alkaline earth sulfonate is magnesium or calcium alkyl aromatic sulfonate having a total base number (TBN, as measured by the procedure of ASTM D2896) ranging from 300 to 400.

Polyvalent metal alkyl salicylate and naphthenate materials may also be included, such as methylene and sulfur bridged materials which are readily derived from alkyl substituted salicylic or naphthenic acids or mixtures of either or both with alkyl substituted phenols. Basic sulfurized salicylates and a method for their preparation are shown in US-A-3595791.

The sulfurized metal phenates can be considered the "metal salt of a phenol sulfide" which thus refers to a metal salt, whether neutral or basic, of a compound typified by the general formula:

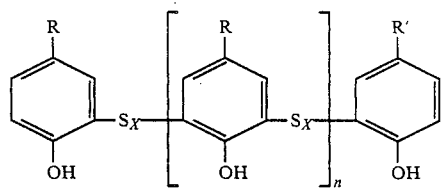

where x =1 or 2, n =0, 1 or 2 or a polymeric form of such a compound, where R is an alkyl radical, n and x are each integers from 1 to 4, and the average number of carbon atoms in all of the R groups is at least about 9 in order to ensure adequate solubility in oil. The individual R groups may each contain from 5 to 40, preferably 8 to 20, carbon atoms. The metal salt is prepared by reacting an alkyl phenol sulfide with a sufficient quantity of metal containing material to impart the desired alkalinity to the sulfurized metal phenate.

The sulfurized alkyl phenol is converted by reaction with a metal containig material including oxides, hydroxides and complexes in an amount sufficient to neutralize said phenol and, if desired, to overbase the product to a desired alkalinity by procedures well known in the art. Preferred is a process of neutralization utilizing a solution of metal in a glycol ether.

Magnesium and calcium containing additives such as described above although beneficial in other respects can increase the tendency of the lubricating oil to oxidise. This is especially true ot the highly basic sulphonates.

According to a preferred embodiment the invention therefore provides a crankcase lubricating composition also containing from 2 to 8000 parts per million of calcium and/or magnesium.

The magnesium and/or calcium is generally present as basic or neutral detergents such as the sulphonates and phenates, and preferred additives are basic magnesium or calcium sulphonates. Preferably the oils contain from 500 to 5000 parts per million of calcium and/or magnesium from such additives.

These compositions of our invention may be as an alternative or in addition contain other similar metal-containing detergent additives, for example, those containing barium, sodium, potassium or lithium.

The lubricating oil used in the lubricant composition may be a mineral lubricating oil or a synthetic lubricating oil or a mixture thereof. Suitable synthetic oils include diester oils such as di(2-ethyl-hexyl) sebacate, azelate and adipate; complex ester oils such as those formed for dicarboxylic acids, glycols and either monobasic acids or monohydric alcohols; silicone oils; sulfide esters; organic carbonates; hydrocarbon oils and other synthetic oils known to the art. The invention is particularly useful in mineral lubricating oils and has the added benefit that it may allow use of base stock oils that have inferior antioxidant properties to those currently used.

The lubricating compositions of the present invention may and usually will contain other traditional lubricant additives, for example, rust inhibitors such as oleic acid and its derivatives, such as N-oleylsarcosine and oleic acid dimers and trimers, lecithin, sorbitan mono-oleate, dodecyl succinic anhydride or ethoxylated alkyl phenols; pour point depressants such as copolymers of vinyl acetate with fumaric acid esters of coconut oil alcohols; phosphites; and viscosity index improvers such as olefin copolymers or polymethacrylates.

In copper-free oils other antioxidants in addition to the zinc dialkyldithiophosphate are sometimes required to improve the oxidative stability of the oil. These supplementary antioxidants are included especially when the basestock has poor oxidative stability; and typically the supplementary antioxidant is added to the oil in amounts from 0.1-2.5 wt %. The supplementary antioxidants that are used include phenols, hindered-phenols, bis-phenols, and sulphurised phenols, catechol, alkylated catechols and sulphurised alkyl catechols, diphenylamine and alkyl diphenylamines and phenyl-1-naphthylamine and its alkylated derivatives.

The inclusion of small amounts of copper generally removes the need for these supplementary antioxidants. It would, however, still be within the scope of our invention for a supplmentary antioxidant to be included especially for oils operating under particularly severe conditions where the presence of such supplementary antioxidants may be beneficial, provided that substantially no phosphorus is thereby introduced.

Additives for lubricating oils are generally supplied as concentrates in oil for incorporation into the bulk lubricant. The present invention therefore provides concentrates comprising an oil solution containing from 1 to 10 wt % of a compound of general formula I, and preferably also:

(1) from 0.005 to 2 wt % of copper; and optionally (2) from 1 to 50 wt % of an additional oil-soluble sulphur-containing compound; and/or (3) from 0.1 to 20 wt % of an additional bearing corrosion inhibitor; and/or (4) a dispersant selected from the group consisting of:
(a) 0 to 60, e.g. 10 to 60 wt % of an ashless dispersant compound,
(b) 0 to 40, e.g. 3 to 40% of a polymeric viscosity index improver dispersant, although it is usual to add any viscosity index improver separately.

The concentrate may also contain other additives such as the detergents and viscosity index improvers previously described. A particularly preferred concentrate also contains a magnesium and/or calcium containing additive and the invention therefore provides a concentrate which further comprises from 0.002 to 8 wt % of calcium and/or magnesium.

The following Examples are now given, though only by way of illustration, to show certain aspects of the invention in more detail.

COMPARATIVE EXAMPLE I AND EXAMPLE 1

In the following Comparative Example and Example of the invention, formulations are prepared with the combustions and amounts of additives set out in Table 1, with the balance being a diluent oil comprising 0.3 wt % sulphur suitable for lubricating compositions. The additives used are as follows:

A is a dispersant V.I. additive comprising an oil solution containing 21% of a multifunctional ethylene-propylene copolymer and containing 0.29 wt % N.

B is an ashless dispersant comprising a 50 wt % oil solution of borated polyisobutenyl succinimide having a polyisobutenyl radical with a molecular weight of approximately 950 and containing 1.6 wt % N and 0.35 wt % B.

C is an oil solution of an overbased magnesium sulphonate having a TBN of 400 and a magnesium content of 9.2 wt %.

D is an oil solution of copper oleate containing 4 wt % copper.

In the formulation of the invention, the compounds of formula IV is used.

The formulations were tested in the following standard tests:

CEC Rig test for cam and lifter weight loss (mg) is carried out using pegged EN32B steel tappets and induction hardened cast iron cams according to Standard CEC Scuffing Test procedure CEC L.31-T81.

These results show the invention provides a surpising advantage in anti-wear performance, even in the substantial absence of phosphorus.

TABLE 1

| Additives (wt %) | Example: Comparative I | Example 1 |
|---|---|---|
| A | 8.5 | 8.5 |
| B | 3.0 | 3.0 |
| C | 1.6 | 1.6 |
| D | 0.3 | 0.3 |
| IV | — | 2.1 |
| CEC rig-cam and lifter wt loss (mg) | 6229 | 39 |
| Sulphur content (%) | 0.33 | 0.67 |
| Copper content (%) | 0.012 | 0.012 |
| Phosphorus content (%) | 0 | 0 |
| Boron content (%) | 0.01 | 0.12 |

Preparation 1

118g of 2-methyl-pentane-2,4-diol, 61.8g of boric acid, 77.2g of dihydroxy-diethyldisulphide and 137g of toluene were refluxed with a Dean and Stark trap to remove 61ml of water, during which time the temperature rose from 90° C. to 130°C. Toluene was then distilled off and the product of formula IV was isolated by stripping under vacuum.

| | Analysis | |
|---|---|---|
| | Found | Calculated |
| B % | 5.3 | 5.5 |

Preparation 2

Using a similar procedure, butane-1,3-diol (121.3g), boric acid (82.4g) dihydroxyethyl disulphide (102.6g) and toluene (107g) were heated under reflux with Dean and Stark apparatus to remove water (83ml. Calc 72ml).

Toluene was stripped off and the product of formula III was filtered.

|  | Analysis | |
|---|---|---|
|  | Found | Calc. |
| Boron % | 6.3 | 6.1 |
| Sulphur % | 14.7 | 18.0 |

Preparation 3

Using a similar procedure, butan-1,3-diol(122.9g), glyceryl mono-oleate (55.2g), boric acid (92.7g), dihydroxyethyl disulphide (111.5g) and toluene (110g) were heated under reflux to remove 85ml water (calc 81ml). Toluene was stripped off and product filtered.

|  | Analysis | |
|---|---|---|
|  | Found | Calc. |
| Boron % | 5.4 | 5.2 |
| Sulphur % | 15.5 | 16.9 |

Product is a mixture of products of formulae IV and V.

Preparation 4

Preparations 1, 2 and 3 are based on the use of dihydroxyethyl disulphide. The following preparation uses dihydroxyethyl monosulphide:

2-methyl pentane-2,4-diol (118g) boric acid (62g), dihydroxyethyl monosulphide (61g) and toluene (100ml) were heated under reflux to remove water (54ml). The toluene was stripped off and the product filtered. The boron content was found to be 5.3% (Calcium 5.8%).

Comparative Testing

The antioxidant behaviour of the product of formula III was compared versus a sulphur-free borate ester of the formula:

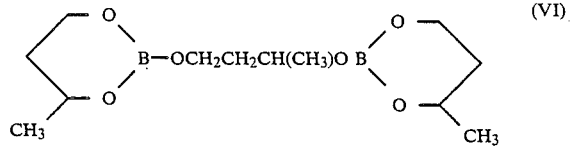

in a lubricant formulated with a polyalphaolefin (PAO) basestock, using an oxidation test in which a 300 gram sample of an oil composition is oxidised by passing 1.7 litres of air per minute through the sample at 165° C. and determining the viscosity at intervals up to 64 hours on a Haake cone-on-plate-viscometer. A further comparison was provided by a similar formulation containing no borate ester.

The formulations tested employed in addition the following components:

PAO = a synthetic lubricant basestock comprising a polyalphaolefin with a kinematic viscosity ($K_v$) at 100° C. =5.50 centistoke; V.I. =132.

E = an olefin copolymer viscosity index improver additive comprising an oil solution of an ethylene-propylene copolymer.

F = an ashless dispersant comprising a 50 wt % oil solution of borated polyisobutenyl succinimide having a polyisobutenyl radical with a molecular weight of approximately 1300 and containing 1.5 wt % N and 0.32 wt % B.

G = an oil solution of an overbased magnesium sulphonate having a TBN of 400 and a magnesium content of 9.2 wt % and a sulphur content of 1.7 wt %.

| Component | Comparison | Invention | Comparison |
|---|---|---|---|
| PAO | 86.6 | 85.6 | 85.6 |
| E | 7.9 | 7.9 | 7.9 |
| F | 4.5 | 4.5 | 4.5 |
| C | 1.0 | 1.0 | 1.0 |
| Cpd III | — | 1.0 | — |
| Cpd VI | — | — | 1.0 |
| Viscosity (cP) at |  |  |  |
| 0 hrs | 51 | 51 | 50 |
| 16 | 109 | 68 | 122 |
| 24 | 183 | 98 | 207 |
| 40 | 300+ | 150 | 300+ |
| 48 |  | 176 |  |
| 64 |  | 251 |  |

These results show that whereas Compound VI give no oxidation stability (if anything giving less stability), the compound of the invention gives greatly improved oxidation stability.

I claim:

1. A sulphur-containing borate ester of the formula:

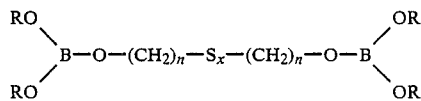

wherein each R is a hydrocarbyl group optionally substituted by one or more —XR″ group, or the two R groups attached to one boron represent a group —(R′$_2$C-)$_m$—X is from 1 to 4, each n is from 1 to 6, each m is from 2 to 4 and each R′ is hydrogen, an —XR″ group, or a hydrocarbyl radical optionally substituted by one or more —XR″ group, X is O, S or NR″ or two groups R′ together form an alicyclic or heterocyclic ring and R″ is hydrogen, a hydrocarbyl radical or a hydrocarbylcarbonyl group.

2. An ester as claimed in claim 1, in which each pair of substituents R represent a —(R′—CH$_2$)$_m$—group and R′ is hydrogen, an alkyl group, or an esterified hydroxy group.

3. An ester as claimed in claim 1, in which the integer n is from 2 to 4 and the integer x is 2.

4. An ester of the formula:

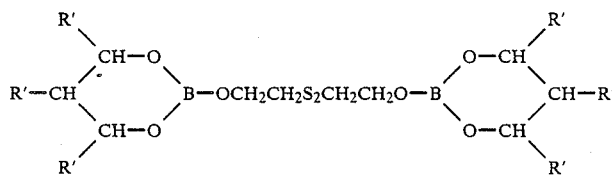

where each R' is independently chosen from hydrogen, alkyl, hydroxy and alkylcarboxy.

5.

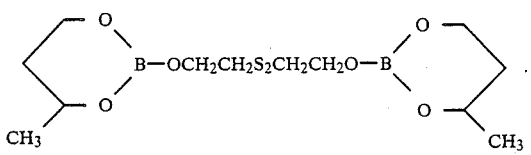

6.

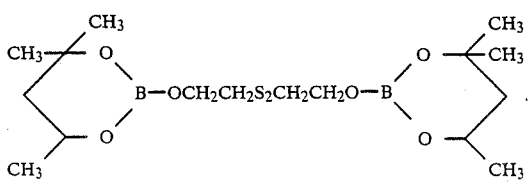

7.

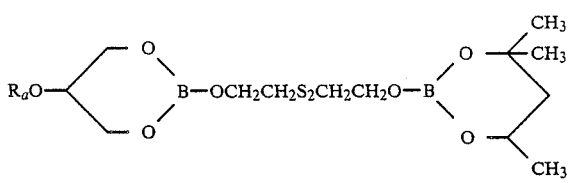

where $R_a$ is an oleoyl group.

8. A process for preparing sulphur-containing borate esters of the formula:

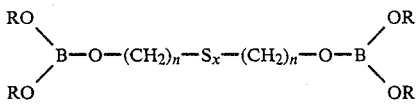

wherein each R is a hydrocarbyl group optionally substituted by one or more —XR" group, or the two R groups attached to one boron represent a group —$(R'_2C)_m$—, x is from 1 to 4, each n is from 1 to 6, each m is from 2 to 4 and each R' is hydrogen, an —XR" group, or a hydrocarbyl radical optionally substituted by one or more —XR" group, X is O, S or NR" or two groups R' together form an alicyclic or heterocyclic ring and R" is hydrogen, a hydrocarbyl radical or a hydrocarbylcarbonyl group, in which a dihydroxy alkyl sulphide of the general formula:

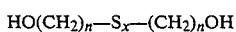

is reacted with one or more appropriate alcohols ROH or diols of the formula HO(R'—CH)$_m$OH and boric acid.

9. A lubricating composition comprising a major amount of oil and at least one sulphur-containing borate ester of the formula:

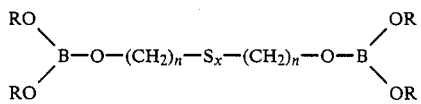

wherein each R is a hydrocarbyl group optionally substituted by one or more —XR" group, or the two R groups attached to one boron represent a group —$(R'_2C)_m$—, x is from 1 to 4, each n is from 1 to 6, each m is from 2 to 4 and each R' is hydrogen, an —XR" group, or a hydrocarbyl radical optionally substituted by one or more —XR" group, X is O, S or NR" or two groups R' together form an alicyclic or heterocyclic ring and R" is hydrogen, a hydrocarbyl radical or a hydrocarbylcarbonyl group.

10. A composition as claimed in claim 9, which contains from 0.01 to 10 wt % of said sulphur-containing borate ester.

11. A lubricant composition comprising a major amount of a lubricating oil, 5 to 500 parts per million by weight of added copper present in oil-soluble form and one or more sulphur-containing borate esters of the formula:

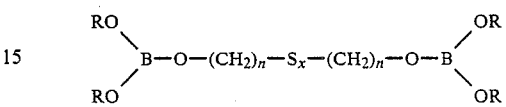

wherein each R is a hydrocarbyl group optionally substituted by one or more —XR" group, or the two R groups attached to one boron represent a group —$(R'_2C)_m$—, x is from 1 to 4, each n is from 1 to 6, each m is from 2 to 4 and each R' is hydrogen, an —XR" group, or a hydrocarbyl radical optionally substituted by one or more -XR" group, X is O, S or NR" or two groups R' together form an alicyclic or heterocyclic ring and R" is hydrogen, a hydrocarbyl radical or a hydrocarbylcarbonyl group.

12. A composition as claimed in claim 11, which contains less than 0.05 wt % phosphorus.

13. A composition as claimed in claim 9, which further comprises from 1 to 10 wt % of an ashless dispersant compound and/or from 0.3 to 10 wt % of a nitrogen or ester containing polymeric viscosity index improver dispersant.

14. A composition as claimed in claim 9, which contains from 2 to 8000 parts per million of calcium or magnesium.

15. A concentrate comprising an oil solution containing from 1 to 10 wt % of at least one sulphur-containing borate ester of the formula:

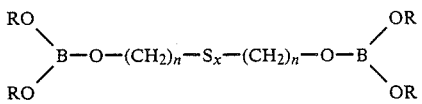

wherein each R is a hydrocarbyl group optionally substituted by one or more —XR" group, or the two R groups attached to one boron represent a group —$(R'_2C)_m$—, x is from 1 to 4, each n is from 1 to 6, each m is from 2 to 4 and each R' is hydrogen, an —XR" group, or a hydrocarbyl radical optionally substituted by one or more —XR" group, X is O, S or NR" or two groups R' together form an alicyclic or heterocyclic ring and R" is hydrogen, a hydrocarbyl radical or a hydrocarbylcarbonyl group.

16. A concentrate as claimed in claim 15, which also contains from 0.005 to 2 wt % of copper.

17. A composition as claimed in claim 16, which further comprises:
(a) from 1 to 50 wt % of an additional oil-soluble sulphur-containing compound; and/or
(b) from 0.1 to 20 wt % of an additional bearing corrosion inhibitor; and/or
(c) 10 to 60 wt % of an ashless dispersant compound.

18. A concentrate as claimed in claim 16, which further comprises from 0.002 to 8 wt % of calcium and/or magnesium.

* * * * *